(12) United States Patent
Murdock et al.

(10) Patent No.: US 10,653,964 B2
(45) Date of Patent: May 19, 2020

(54) TRANSMITTING SENSOR DATA CREATED IN A GAME ENVIRONMENT TO A SET OF PROCESSORS OUTSIDE THE GAME ENVIRONMENT BASED ON PREDEFINED EVENT DETERMINATIONS

(71) Applicants: Wilbert Quinc Murdock, Bronx, NY (US); Philip Alister Williams, Salt Point, NY (US)

(72) Inventors: Wilbert Quinc Murdock, Bronx, NY (US); Philip Alister Williams, Salt Point, NY (US)

(*) Notice: Subject to any disclaimer, the term of this patent is extended or adjusted under 35 U.S.C. 154(b) by 0 days.

(21) Appl. No.: 15/466,569

(22) Filed: Mar. 22, 2017

(65) Prior Publication Data
US 2017/0282081 A1    Oct. 5, 2017

Related U.S. Application Data

(60) Continuation-in-part of application No. 12/799,529, filed on Apr. 26, 2010, now Pat. No. 9,662,558, (Continued)

(51) Int. Cl.
*A63F 13/79* (2014.01)
*A63F 13/812* (2014.01)
(Continued)

(52) U.S. Cl.
CPC ............ *A63F 13/79* (2014.09); *A63B 57/405* (2015.10); *A63B 67/02* (2013.01); *A63B 69/36* (2013.01); *A63B 69/3632* (2013.01); *A63F 13/21* (2014.09); *A63F 13/812* (2014.09); *A63F 13/87* (2014.09); *A63B 53/04* (2013.01); *A63B 57/357* (2015.10); *A63B 69/3655* (2013.01); *A63B 69/3658* (2013.01); *A63B 69/3676* (2013.01); *A63B 69/3685* (2013.01); *A63B 69/3688* (2013.01); *A63B 71/0616* (2013.01); *A63B 71/0622* (2013.01); *A63B 71/0669* (2013.01); *A63B 71/0686* (2013.01); *A63B 2069/362* (2013.01); *A63B 2071/063* (2013.01); *A63B 2071/065* (2013.01); *A63B 2071/0647* (2013.01); *A63B 2220/00* (2013.01); *A63B 2220/13* (2013.01); *A63B 2220/16* (2013.01); *A63B 2220/30* (2013.01);
(Continued)

(58) Field of Classification Search
CPC . A63B 24/0021; A63B 24/0084; A63B 67/02; A63B 69/36; A63B 69/3632; A63B 69/3655; A63B 69/3658; A63B 69/3676; A63B 69/3685; A63B 69/3688; A63B 71/0616; A63B 2220/83; A63B 2220/833
See application file for complete search history.

(56) References Cited

U.S. PATENT DOCUMENTS

| | | | | |
|---|---|---|---|---|
| 5,128,671 A | * | 7/1992 | Thomas, Jr. | ............ A63F 13/06 341/20 |
| 5,209,483 A | * | 5/1993 | Gedney | .............. A63B 69/0026 473/223 |

(Continued)

*Primary Examiner* — William H McCulloch, Jr.
(74) *Attorney, Agent, or Firm* — Robert DeWitty; DeWitty and Asociates, Chtd.

(57) ABSTRACT

The invention relates to a system that connects a game implement to a computer. Two or more persons are allowed to be interconnected and play interactively through the system.

21 Claims, 16 Drawing Sheets

Related U.S. Application Data which is a division of application No. 09/570,233, filed on May 12, 2000, now Pat. No. 7,789,742.

(60) Provisional application No. 60/133,722, filed on May 12, 1999.

(51) Int. Cl.

| | | |
|---|---|---|
| *A63F 13/87* | (2014.01) | |
| *A63F 13/21* | (2014.01) | |
| *A63B 69/36* | (2006.01) | |
| *A63B 67/02* | (2006.01) | |
| *A63B 57/40* | (2015.01) | |
| *A63B 71/06* | (2006.01) | |
| *A63B 57/30* | (2015.01) | |
| *A63B 53/04* | (2015.01) | |

(52) U.S. Cl.
CPC ....... *A63B 2220/53* (2013.01); *A63B 2220/62* (2013.01); *A63B 2220/801* (2013.01); *A63B 2220/803* (2013.01); *A63B 2220/833* (2013.01); *A63B 2220/89* (2013.01); *A63B 2225/20* (2013.01); *A63B 2225/50* (2013.01)

(56) References Cited

U.S. PATENT DOCUMENTS

| | | | | |
|---|---|---|---|---|
| 5,221,088 A * | 6/1993 | McTeigue | A63B 24/0003 | 434/252 |
| 5,524,637 A * | 6/1996 | Erickson | A61B 5/1038 | 600/592 |
| 5,592,401 A * | 1/1997 | Kramer | A63B 69/3608 | 340/524 |
| 5,611,731 A * | 3/1997 | Bouton | A63F 13/02 | 463/37 |
| 5,700,204 A * | 12/1997 | Teder | A63B 24/0021 | 473/199 |
| 5,702,323 A * | 12/1997 | Poulton | A63B 24/00 | 434/247 |
| 5,779,549 A * | 7/1998 | Walker | A63F 13/12 | 463/42 |
| 5,792,000 A * | 8/1998 | Weber | A63B 24/0003 | 473/223 |
| 5,902,968 A * | 5/1999 | Sato | G06F 3/03545 | 178/19.01 |
| 5,982,352 A * | 11/1999 | Pryor | G01S 5/16 | 345/156 |
| 6,028,593 A * | 2/2000 | Rosenberg | A63F 13/10 | 345/156 |
| 6,069,594 A * | 5/2000 | Barnes | G01S 5/186 | 345/156 |
| 6,073,086 A * | 6/2000 | Marinelli | A63B 43/00 | 473/198 |
| 6,162,123 A * | 12/2000 | Woolston | A63F 13/10 | 273/148 B |
| 6,206,745 B1 * | 3/2001 | Gabai | A63H 3/28 | 446/175 |
| 6,230,081 B1 * | 5/2001 | Albertshofer | G01C 22/004 | 235/375 |
| 6,254,492 B1 * | 7/2001 | Taggett | A63B 24/0003 | 473/219 |
| 6,466,232 B1 * | 10/2002 | Newell | G06F 1/163 | 345/3.1 |
| 6,537,076 B2 * | 3/2003 | McNitt | A63B 24/0003 | 434/247 |
| 6,720,949 B1 * | 4/2004 | Pryor | A63F 13/02 | 345/158 |
| 7,095,312 B2 * | 8/2006 | Erario | A63B 24/0021 | 340/323 R |
| 7,789,742 B1 * | 9/2010 | Murdock | A63B 24/0021 | 463/3 |
| 7,789,767 B2 * | 9/2010 | Lindsay | A63B 24/0021 | 473/150 |
| 8,133,124 B2 * | 3/2012 | Braun | H04N 7/17318 | 473/131 |
| 8,303,311 B2 * | 11/2012 | Forest | G06Q 10/10 | 434/252 |
| 8,425,350 B2 * | 4/2013 | Savarese | A63B 24/0021 | 156/145 |
| 8,861,091 B2 * | 10/2014 | French | A63B 24/0003 | 359/629 |
| 9,028,338 B2 * | 5/2015 | Chiono | A63B 69/3661 | 473/226 |
| 9,457,228 B2 * | 10/2016 | Sinha | H04N 5/772 | |
| 9,662,558 B2 * | 5/2017 | Murdock | A63B 24/0021 | |
| 9,802,129 B2 * | 10/2017 | Murdock | A63F 13/92 | |
| 2002/0036617 A1 * | 3/2002 | Pryor | G06F 3/042 | 345/156 |
| 2003/0017890 A1 * | 1/2003 | McDonald | A63B 57/00 | 473/407 |
| 2005/0171410 A1 * | 8/2005 | Hjelt | A61B 5/00 | 600/300 |
| 2007/0167247 A1 * | 7/2007 | Lindsay | A63B 24/0021 | 473/131 |
| 2008/0076580 A1 * | 3/2008 | Murdock | A63B 24/0021 | 463/42 |
| 2008/0188310 A1 * | 8/2008 | Murdock | A63B 69/3632 | 463/42 |
| 2009/0036237 A1 * | 2/2009 | Nipper | A63B 24/0021 | 473/409 |
| 2011/0081978 A1 * | 4/2011 | Murdock | A63B 24/0021 | 473/191 |
| 2011/0082571 A1 * | 4/2011 | Murdock | A63B 24/0021 | 700/92 |
| 2011/0087344 A1 * | 4/2011 | Murdock | A63B 24/0021 | 700/91 |
| 2011/0092260 A1 * | 4/2011 | Murdock | A63B 24/0021 | 463/3 |
| 2011/0130223 A1 * | 6/2011 | Murdock | A63B 24/0021 | 473/409 |
| 2011/0151977 A1 * | 6/2011 | Murdock | A63B 24/0021 | 463/42 |
| 2011/0212757 A1 * | 9/2011 | Murdock | A63B 24/0021 | 463/2 |
| 2011/0281621 A1 * | 11/2011 | Murdock | A63B 24/0021 | 463/3 |
| 2012/0220385 A1 * | 8/2012 | Richardson | A63B 24/0021 | 473/156 |
| 2016/0354660 A1 * | 12/2016 | Kostuj | G09B 19/0038 | |
| 2017/0004729 A1 * | 1/2017 | Kano | G09B 19/0038 | |
| 2017/0282081 A1 * | 10/2017 | Murdock | A63F 13/79 | |

* cited by examiner

TRANSMITTING SENSOR DATA CREATED IN A GAME ENVIRONMENT TO A SET OF PROCESSORS OUTSIDE THE GAME ENVIRONMENT BASED ON PREDEFINED EVENT DETERMINATIONS

PRIORITY CLAIM

This application is a continuation-in-part of U.S. patent application Ser. No. 12/799,529, filed Apr. 26, 2010, which is a divisional and claims the benefit and priority of U.S. patent application Ser. No. 09/570,233, filed May 12, 2000, both of which, in turn, claims the benefit and priority of U.S. provisional patent application 60/133,722, filed May 12, 1999. The above referenced applications are incorporated herein by reference as if restated in full.

BACKGROUND

Players of tournament games require a network to enable them to play with one another remotely. But, in order for play to occur simultaneously, players must be informed that a game is ongoing or underway. Similarly, if one player wishes another player to join, the one player must invite the other, by in part, informing the other player of the time and location of play as well as information specific to the game the one player is participating in or forming. Accordingly, a communication means is required to bring players together. A communication means for remote players does not exist for players of real-world games where players use physical instruments where game data is based at least in part on sensor-acquired data.

SUMMARY

This invention relates to a system that interconnects a golf club or other sports implements to a computer. From hereon, sports equipment, sports equipment items, is an example of a gaming unit, tool, or item, and the latter should be understood to be included in the former. In a preferred embodiment, the computer is coupled wirelessly to a sports implement component. Further, the invention, with components summarized below, allows participants to be paired or grouped together to enter into a game competition against each other. Each player asks the computer who is available to play a contest via the Internet to the game server. Once a player pairs up against another player anywhere in the world and play ensues, each local computer display shows each participants score via animation or graphics that preferably relate to a player's individual performance statistics. A single player may play without an opponent to practice and improve basic sports skills using the computer and display to track performance.

A wireless piece of sporting equipment is constructed to contain, or alternatively a standard piece of sporting equipment is modified to contain, multiple sensors or transducer array located on the surface of said smart sports equipment or gaming tool or sports implement and GPS sensing circuitry, and a gyroscope. Moreover, a gyroscope is hereon and heretofore understood to be synonymous with a gyrometer and the latter is understood to be included in the former.

In one embodiment, the sporting equipment is a hockey stick, coupled with a hockey puck, race car steering wheel coupled with a driver's hand, bow coupled with an arrow, boxing gloves coupled with a fist, tennis racket, coupled with a tennis ball, basketball ball coupled with a shooting hand, football coupled with a throw, bicycle coupled with a pedal, bowling ball coupled with a bowling throw, soccer coupled with a kick, volleyball coupled with a hitting hand, baseball bat coupled with a baseball, all using sensors including accelerometers, gyroscopes and a compass and or a combination of multiple sensing devices. It should be noted that sports like football would require a sensor based football and sensors on the hand of the quarterback for a full range of interactive data. As an example upon impact of the tennis racket with a tennis ball, or impact of the baseball bat with a baseball, the impacted sensors produce detectable variances representing the magnitude and duration of the racket-ball impact force or baseball impact force and the proximate location of such contact relative to the preferred location, the "sweet spot", on the face of the tennis racket or baseball bat. The variances are electronically processed into digitally coded information and remotely transmitted by an electrical communication circuit either contained within or attached to the tennis racket or sports implement.

The system responds to a predefined event occurring within a gaming environment by automatically transmitting an alert or message outside the gaming environment, comprising: a game server, that includes a processor and a memory storing a number of machine instructions: the game server being included within a gaming service that established the gaming environment and further including a communication interface that couples the game server to a network, and the processor executes the machine instructions stored in the memory, causing the processor to carry out a number of functions, including: detecting when a predefined event occurs within the gaming environment, the gaming environment provides a secure and limited access such that players only gain access to the gaming environment through a secure gateway, the secure gateway is inaccessible by any person communicating over a network that is outside of the gaming environment, and the network is accessible from within the gaming environment by players participating in the gaming environment, and in response to detecting the predefined event, initiating transmission of an alert or message to a person outside the gaming environment over the network.

The system further comprising an alerts service having a server that includes a communication interface, a memory, and a processor coupled to a communication interface and the memory of the alert server, the processor of the alert server executes the machine instructions stored in the memory of the alert server to carry out a further number of functions, including receiving at least an indicia of information to be included in the alert or message transmitted from the game server and in response, transmitting the alert or message to a person outside the gaming environment over the network. The system sends the alert or message which is transmitted over the network as an email. The system sends the alert or message which is transmitted over the network to a communication system that re-transmits the alert or message to a portable communication device. The system's machine instructions stored in the memory of the game server further cause the processor of the game server to map an identifier of the person within the gaming environment to a corresponding identifier that is used to identify that person on the network so that the alert message will be sent to that person by the alert server outside the gaming environment. Moreover, a computer or equivalently a computer processor is hereon and herefore understood to be, or comprise, a microcontroller and or a microporcessor, and each of the latter is understood to be included in the former.

The system's execution of the machine instructions causes the game server to detect that the predefined event has occurred when a player gains access to the gaming environment, execution of the machine instructions causes the processor to initiate transmittal of information identifying the player to at least one person who is on a list of the player, where the list is stored in the memory. The systems alert or message comprises an invitation to at least one person to access the gaming environment and participate in playing a game thereon with the player. The systems information included in the alert or message relates to billing a player for services rendered in the gaming environment. The systems information included in the alert or message refers to a change in a gaming content within the gaming environment. The systems information included in the alert or message is a reminder to a player to play a previously scheduled game within the gaming environment.

The system's execution of machine instructions further causes the processor to enable a person to select at least one form in which alerts or messages will be transmitted in response to the predefined event, at least one said form being selectable from a plurality of different forms. The system's number of forms include an email, a pop-up that is displayable, and a message perceivable on a portable communication device that is coupled to a communications system.

A system for interactive processing wherein the system comprises a number of sports equipment, wherein each sports equipment is provided with sensors such that a set of sensor data related to the game equipment is captured, and each sports equipment also comprises a communication device associated with the sports equipment for establishing a communication link with an Internet server, wherein the Internet server is provided with an application that is arranged to relate the data transferred from different game equipment to one another. The system sensor is capable of capturing at least one type of data selected from the group comprising data, which are characteristic of the movement of the sports game equipment, physiological data of the user of the sports game equipment, and data describing the spatial orientation and the position of the sports game equipment.

The System, wherein the sports game equipment includes a clock generating a time signal and electronic processing associating the sensor data with the time signal. The System, wherein one of the sports equipment comprises a number of sensors including a location sensor. The System, wherein one of the sports equipment includes a storage to store the sensor data wherein the sports equipment are provided with a clarification means allowing identification from which sports equipment sensor data are transmitted to the Internet Server. The System wherein the communications link between the sports equipment and the Internet Server comprises a base station. The System wherein the application is designed to assign data received from different sports equipment to different user accounts. The System wherein the application generates output data to drive a display device to visualize sensor data.

A wireless golf club is constructed to contain, or alternatively, a standard golf club is modified to contain a multiple sensor or transducer array located on the club head at the face or hitting surface. Upon impact of the head of the club with a golf ball, the impacted sensors produce detectable variances representing the magnitude and duration of the club-ball impact force and the proximate location of such contact relative to the preferred location, the "sweet spot" on the face of the club head. The variances are electronically processed into digitally coded information and remotely transmitted by an electrical communication circuit either contained within or attached to the golf club.

In each golf club device and golf ball receptacle device according to this invention, in a preferred embodiment the transducers are or include piezoactive elements and or pressure sensors. As used herein, "piezoactive" includes piezoelectric and piezoresistive components. Piezoactive components are defined as components with the electrical properties of which, when the component is subjected to physical force, vary.

The smart golf club system uses biofeedback to create an intelligent golf training and entertainment system. The smart golf club system is a diagnostic and analysis tool used to improve a player's skills by utilizing relatively instantaneous visual cues and acoustic feedback with little or no human intervention. The smart golf club system takes the generated data and reconstructs it into a useful visual format that can be presented in a variety of ways including 3-dimensional animation.

The smart golf club system integrated circuit or circuits can be located anywhere within the club including the head and or shaft.

The smart golf club has a means via its built-in microcontroller to process, analyze, store, hitting pattern data and transmit it to the local computer and or the Internet for further analysis. In playback mode the smart golf club system memorizes the number of times each sensor was struck. This provides the golfer information about his or her hitting pattern. Using a computer algorithm, we can analyze and calculate a hitting pattern and resulting in a personalized sports hitting detection system for each athlete.

The ball receptacle has an open end to receive a golf ball and contains a transducer located so as to sense the ball entering the receptacle. Upon impact with the golf ball, the sensor produces a detectable variance representing impact with the ball. The variance is electronically processed into display coded information and remotely transmitted by an electrical communication circuit. In one preferred embodiment the communication circuit is contained within the receptacle. Preferably, the communications circuit for the receptacle is a radio frequency transmitter. The receptacle can either be designed for indoor use or can be a cup in an actual green with the communication circuit housed in the cup or elsewhere.

In each of the golf club device and golf ball receptacle device according to this invention, in a preferred embodiment the transducers are or include piezo-active elements.

The golf club swing motion sensing device contains an array of uniformly distributed sensing transducers upon or proximate to the device surface. This motion sensing device may be formed as a mat, a plate, or other substantially flat surface or simply a surface from which a golf ball is hit. The transducers produce detectable varying characteristics such as capacitance representing the velocity, angle, and proximity of a golf club relative to the surface of the device. The variances are electronically processed into digitally coded information and remotely transmitted by an electrical communication circuit contained within or electronically connected to the device.

At each remote player site, wireless radio frequency equipment receives the digitally coded transmitted signals from the golf club, the golf ball receptacle, and the club swing motion sensing device. The signals are demodulated and processed into serial binary data suitable for communications to the local computer via either serial or parallel ports. As the game progresses, the computer under the control of the game software, monitors and directs the flow of communications between the players via the internet and displays the game simulations and performance information.

At each remote player site, a computer under the control of the game software, monitors and controls the sequential play of the game and interacts with the player at the site and also competing players at the other remote sites via the internet. The software system generates the game simulations for display and tracks each player's performance as the game progresses.

The above, and further features and advantages of the invention will be better understood with reference to the accompanying drawings and the following detailed description of preferred embodiment.

While the word ball is used in this disclosure, it should be understood that any kind of projectile shall suffice for the purpose of this disclosure.

DETAILED DESCRIPTION OF THE DRAWINGS

Figure 1:
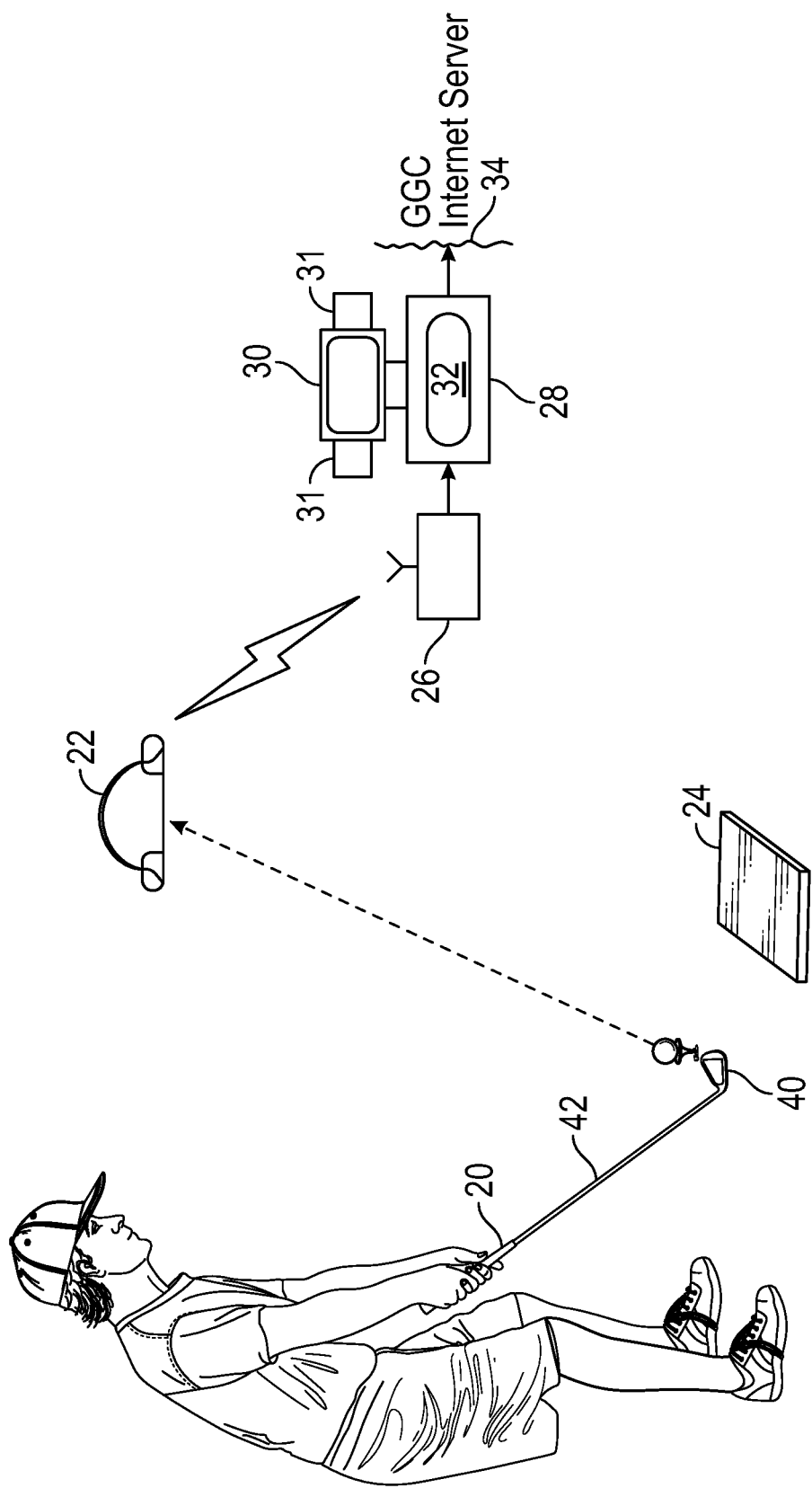
FIG. 1 is a diagrammatic illustration of components of a computer implemented golf system according to this invention.

As shown in FIG. 1, a preferred embodiment of the invention includes a wireless smart golf club 20, a wireless golf ball receptacle 22, a wireless golf club motion sensing plate 24, a wireless receiver 26 connected to a computer 28, and a display or monitor 30 with speakers 31 operated under the control of golf system software 32, and connected via the Internet to an Internet golf game server 34 (called herein the GGC server)

Figure 2:
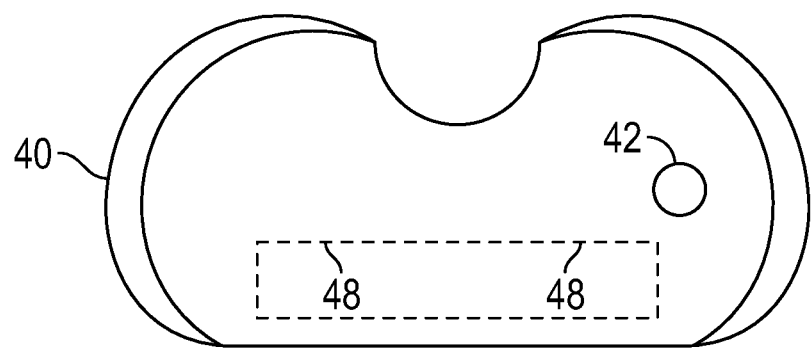
FIG. 2 is a top plan view of a golf club with sensors and circuitry and used in the computer implemented system of FIG. 1.
Figure 3:
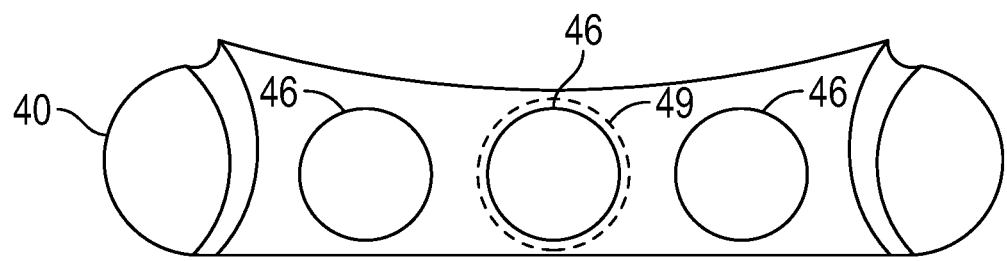
FIG. 3 is a front elevation view of the golf club head of FIG. 2, and shows three sensors located at the face of the club head.

The smart golf club 20 has a head 40 and a shaft 42. As shown in FIGS. 2 and 3, the head 40 has a shaft opening 42, a plurality of embedded contact sensors 46 (three are illustrated in the preferred embodiment), and the internal electronics circuitry 48 including a wireless radio frequency transmitter (58 in FIG. 5). As shown, at least one of the sensors 46 is located at or proximate to the optimal location on a club face 47 for contact with the golf ball, the "sweet spot" 49. The remaining two sensors are adjacent and on either side of the sweet spot 49. The contact sensors may be, but are not limited to sensors employing piezoactive type transducers, specifically, either piezo-electric or piezo-resistive transducers (similar, but is not limited to the Cooper Instruments LPM 562).

Figure 3A:
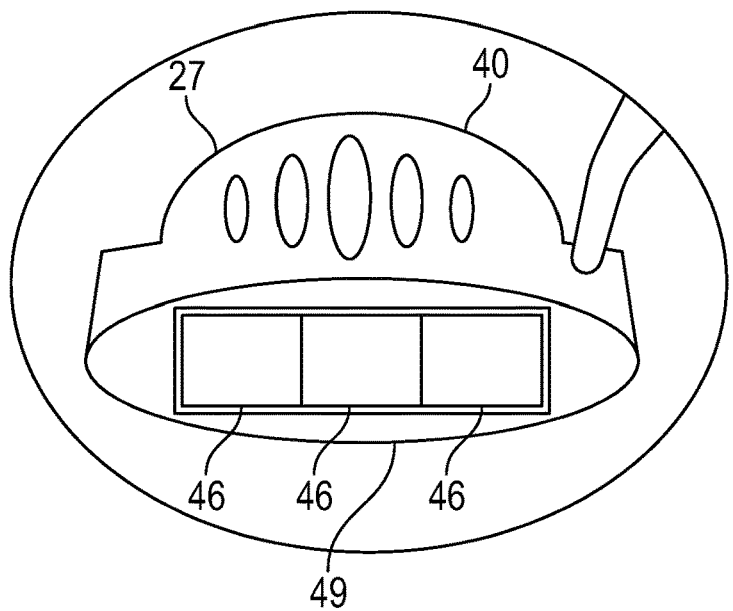
FIG. 3A is a front plan view of a further embodiment of a club head for us with the computer implemented golf system of FIG. 1.

In an alternative embodiment, FIG. 3A, three sensors 46 are applied to the face of an adapted club by a Mylar tape or other means 49. Again, the electronic circuitry is internal to the club-head 40 and connects to the sensors 46 by leads 27.

Figure 4:
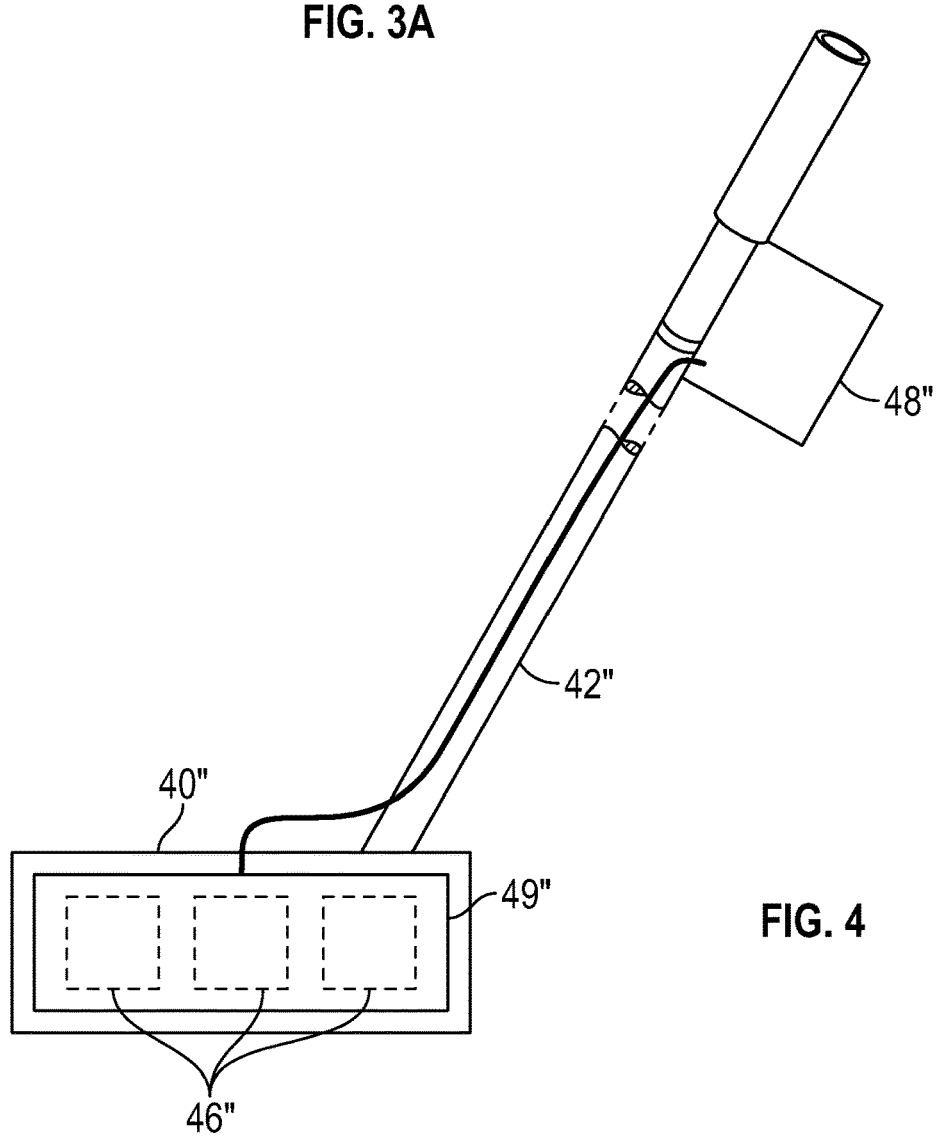
FIG. 4 is a diagrammatic front plan view of a putter with a club head and circuitry forming a further, alternative embodiment of a club for use with the computer implemented system of FIG. 1.

In a second alternative embodiment, to retrofit a standard golf club, contact sensors 46 are part of an adapter 40 attached to an ordinary club head as seen in FIG. 4, and wire connected to an electronic circuitry 48 attached to the club shaft 42 or elsewhere on the club.

Figure 5:
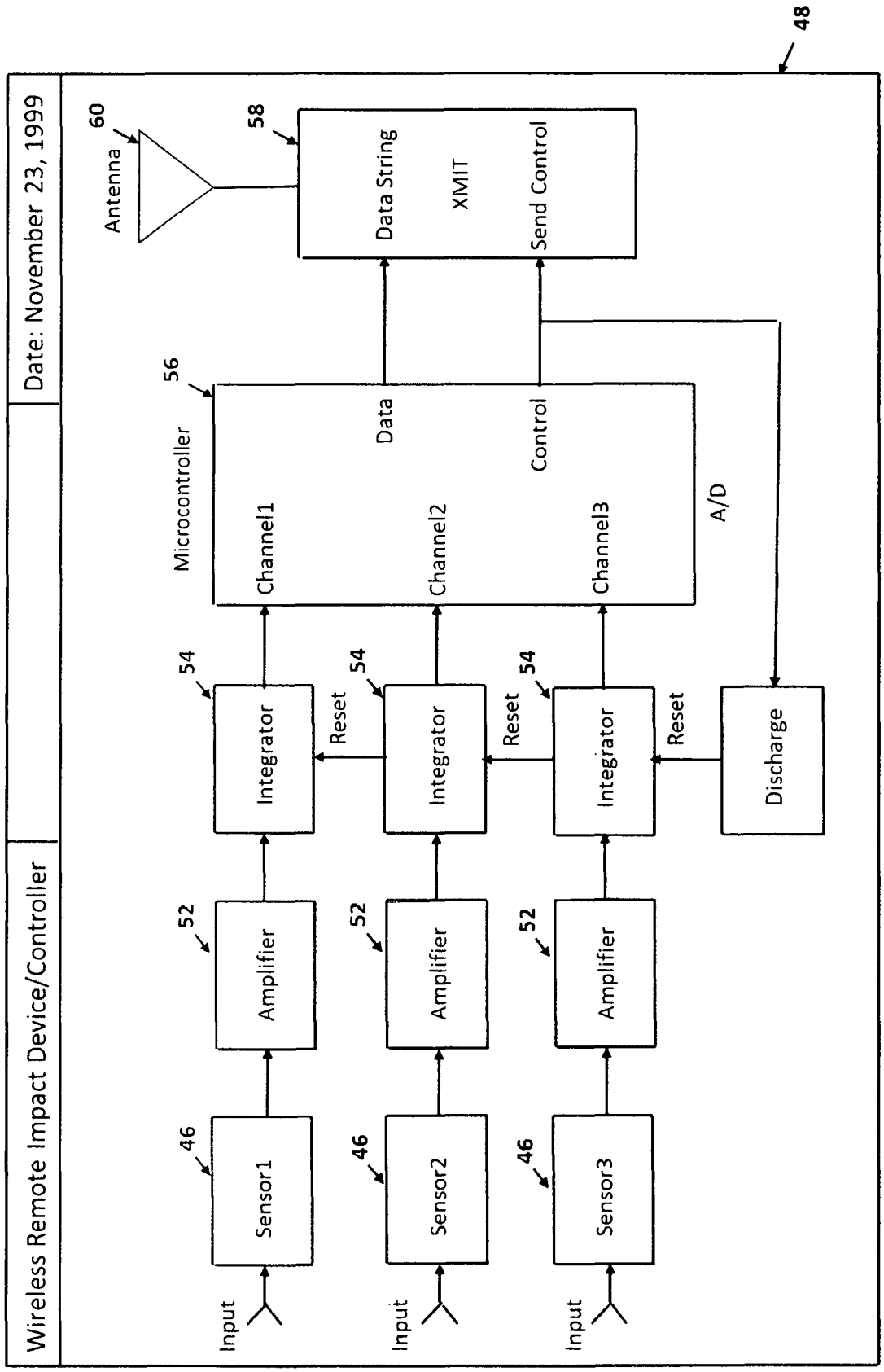
FIG. 5 is a schematic block diagram of a club head electronics installation for use with the club heads of FIGS. 2-4.

A golf ball contacting any sensor 46 produces a detectable variance indicating the magnitude and duration of sensor-ball impact. The variance may be a change in resistance of a piezo-resistive transducer or a voltage change in the case of a piezo-electric transducer. As shown in FIG. 5, the variance is detected and amplified by an associated amplifier 52 and is the input to an associated integration circuit 54, the output of which represents the energy and impulse of the ball-club contact event. Connected to the integration circuit 54, a microcontroller 56 is a multi-input signal processing circuit (similar, but not limited to a NXP MC9S08) having analog to digital signal converting circuits (ADCs), one for each input channel, and a sequential digital signal encoding circuit connected so as to convert the ADC outputs into a time multiplexed serial digital data stream containing a binary-coded word for each channel indicating the energy of the associated sensor-ball impact event.

The radio frequency transmitting circuit 58 receives the serial digital data from the microcontroller 56 and wirelessly transmits the information via an internal antenna 60 to a receiver 26 (FIG. 1) for subsequent processing by the computer 28.

Figure 6A:
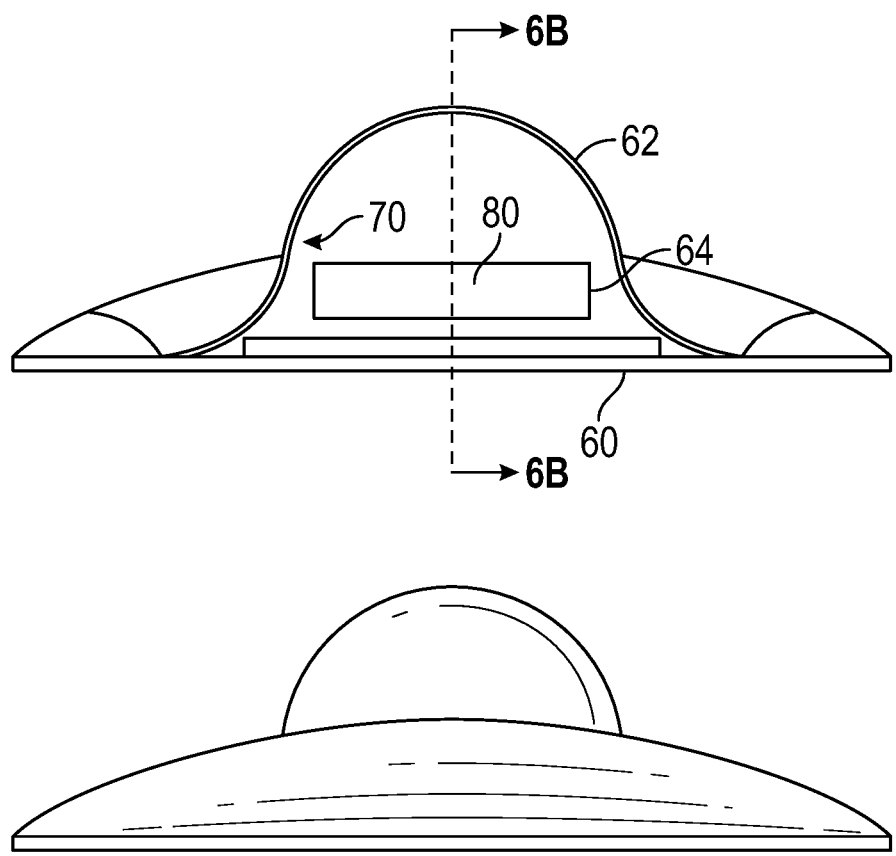
FIG. 6A is a front elevation view of a golf ball receptacle for use with the system of FIG. 1.
Figure 6B:
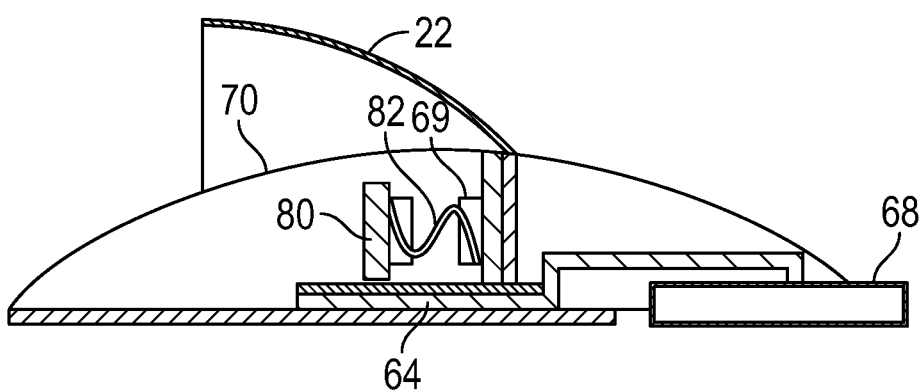
FIG. 6B is a cross-sectional view along the lines B-B of FIG. 6A.
Figure 6C:
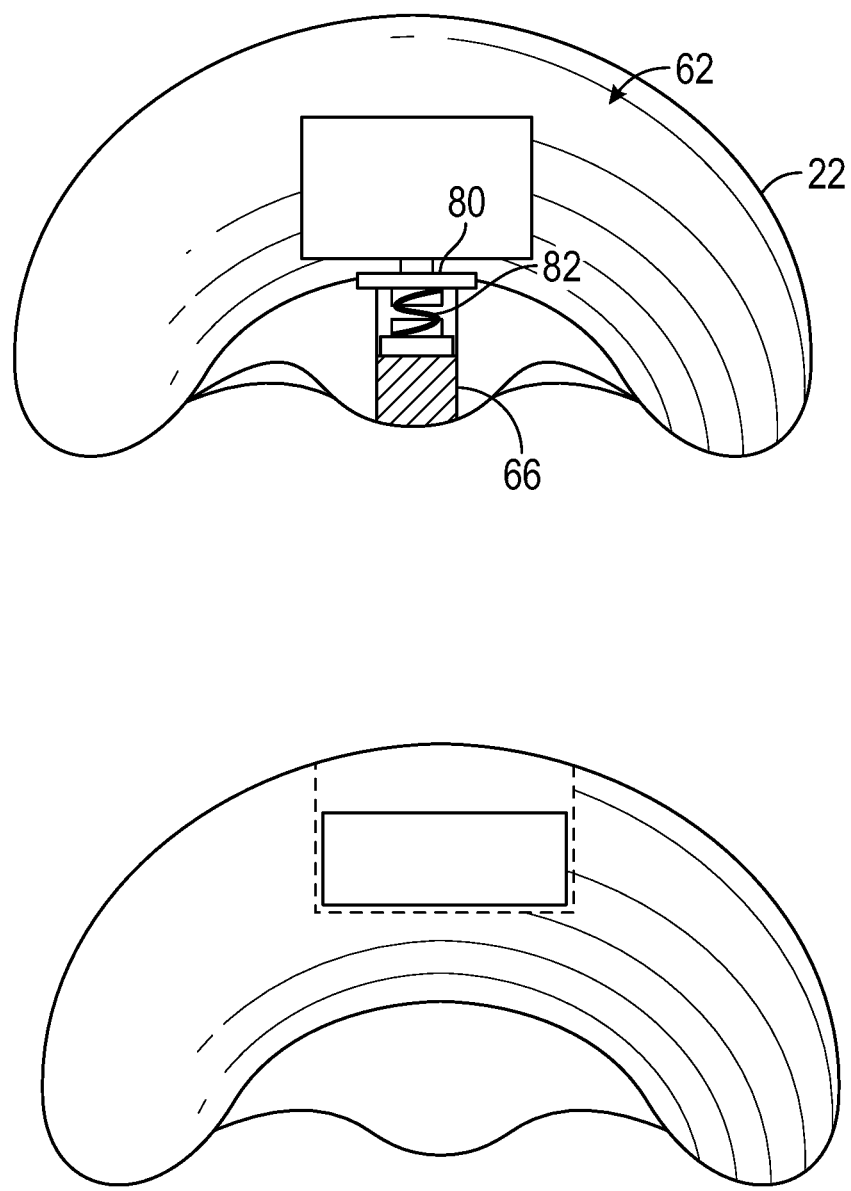
FIG. 6C is a fragmentary top plan view of the receptacle of FIGS. 6A and 6B illustrating internal components of the receptacle.
Figure 7:
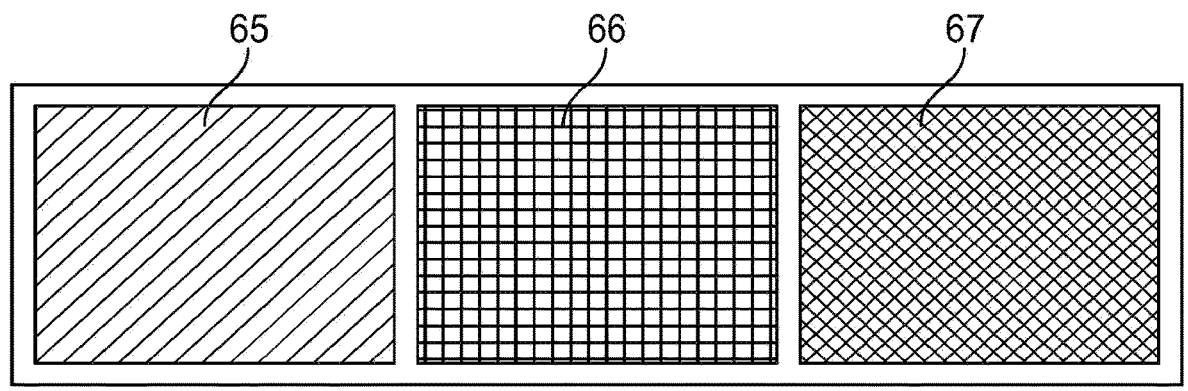
FIG. 7 is a top plan view of a golf ball sensing element with three distinct activation areas for use in the receptacle of FIGS. 6A-6C.

The golf ball receptacle 22 has a top 62 shaped to allow entry of a golf ball, as shown in FIGS. 6A, 6B, and 6C. The receptacle has a contact sensor pad 64, shown in FIG. 7, containing at least one contact sensor (three different activation areas 65, 66, and 67 are illustrated in the preferred embodiment), a ball return mechanism 69 (FIG. 6B) and internal electronic circuitry 68 (FIG. 68). The internal circuitry includes a wireless radio frequency transmitter (not separately shown in FIGS. 6A, B and C). As shown, the preferred embodiment has contact sensor pad 64 positioned within the receptacle 60 such that the center activation area 66 aligns with the center of a ball entry 70. Additional sensor activation area 65 and 67 are adjacent, one on either side of the center area 66. In the preferred embodiment, of FIGS. 6A, 6B, and 6C, and like the sensor used at the face of the club, the sensors may be, but are not limited to, sensors employing piezo-active type transducers, specifically, either piezo-electric or piezo-transducers.

Figure 8:
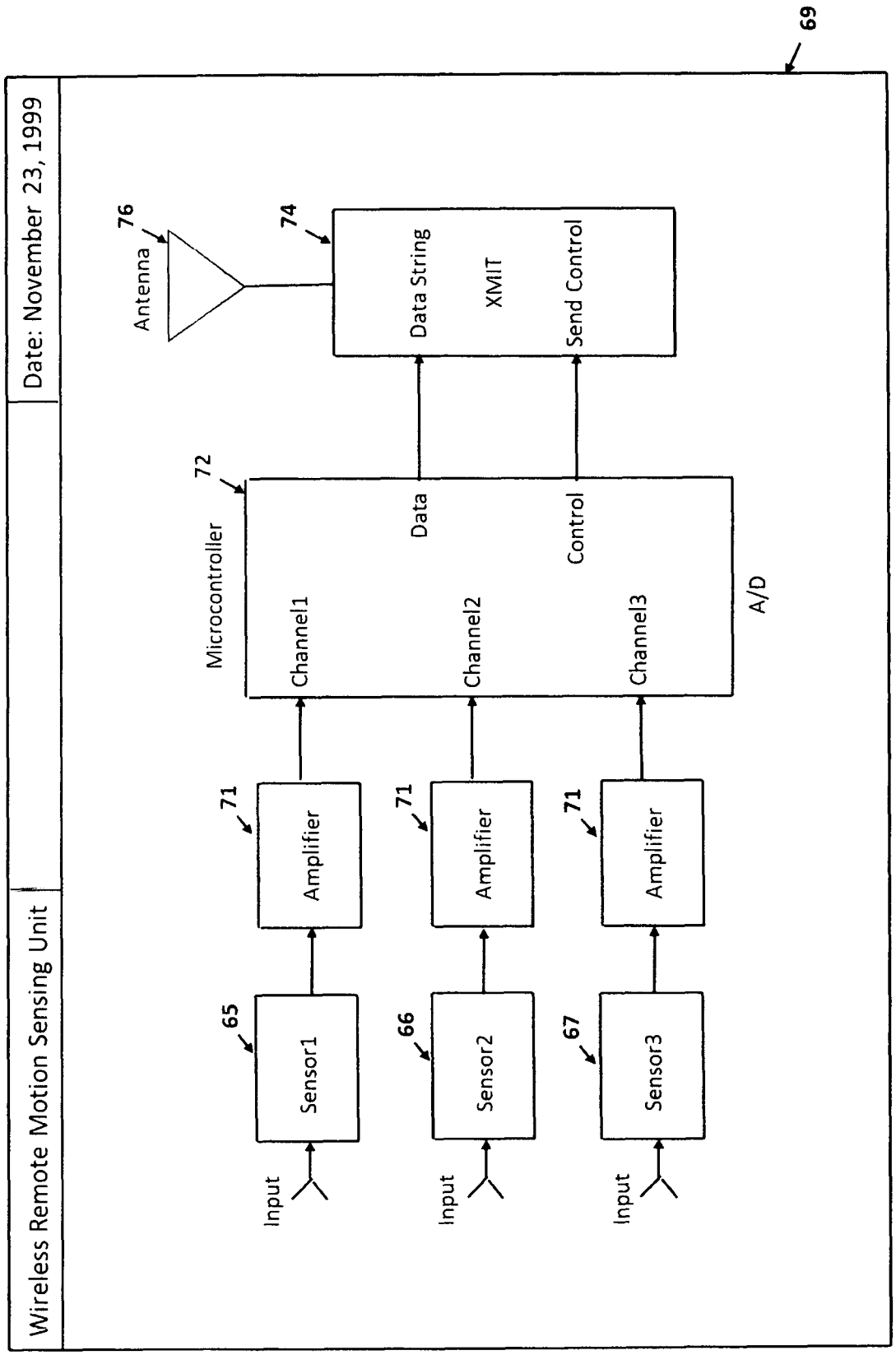
FIG. 8 is a schematic block diagram of a receptacle electronics installation for communicating with the computer in a computer implemented system according to FIG. 1.

A golf ball entering the receptacle 60 and containing the sensor pad 65, 66 or 67 produces a detectable variance indicating the ball entry event. The variance may be a change in resistance in the case of a piezo-resistive transducer (similar, but not limited to Cooper instruments LPM 562) or a voltage change in the case of a piezo-electric transducer. As illustrated in FIG. 8, the variance is detected and amplified by an associated amplifier 71. The amplified signal then is input to a microcontroller 72 having an analog to digital signal converting circuit (ADC) and a digital signal encoding circuit connected so as to convert the ADC output representing the sensors signals into a serial digital data stream containing a binary coded word indicating the sensor-ball contact event. The microcontroller 72 may be the same or similar to the microcontroller 56 of the golf club electronics. A radio frequency transmitter circuit 74 receives the serial digital data from the microcontroller 72 and wirelessly transmits the information via an internal antenna 76 to the receiver 26 (FIG. 1) for subsequent processing by the computer 28.

The ball return mechanism 68 can be simple as a back plate 80 located to be engaged by a golf ball entering the receptacle 22 and supported and biased by a spring or springs 82 to eject the ball. Other known ejection devices, similar to those used in pinball machines and either mechanically, or even electrically activated, can be used to improve the effect if desired.

The receptacle configuration is susceptible to much variation. The receptacle illustrated and described above is well suited to indoor use, on carpet for example. It is clear, however, that an actual cup, installed in an actual green, with real or synthetic grass, can be similarly equipped.

Figure 9A:
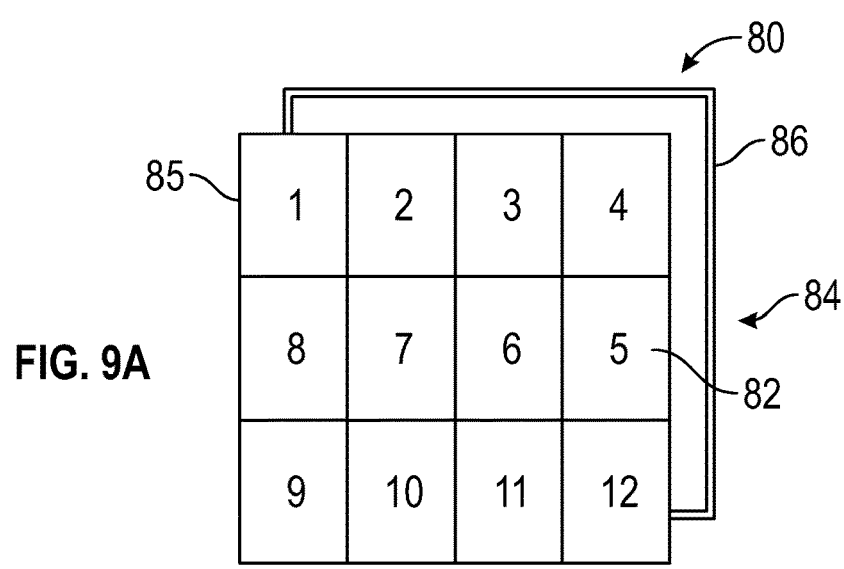
FIGS. 9A-9D are diagrammatic illustrations of a golf club motion or swing sensor plate for use with the system according to FIG. 1.
Figure 9B:
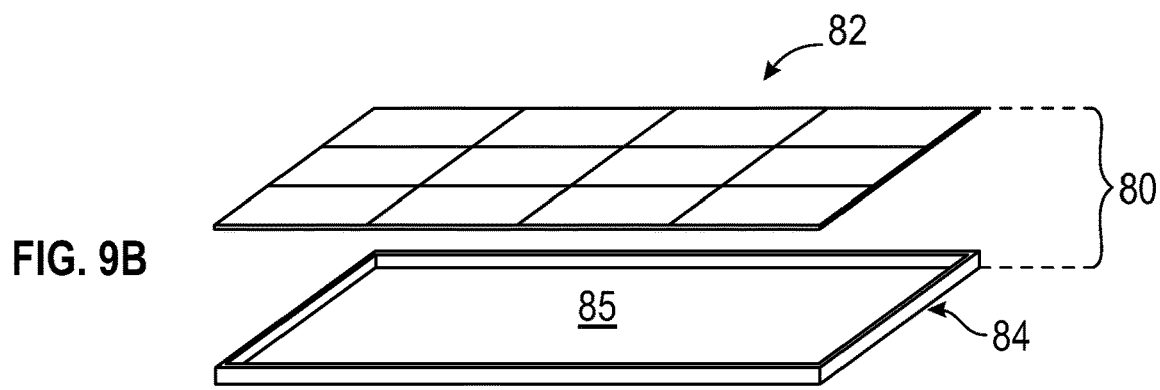
Figure 9C:
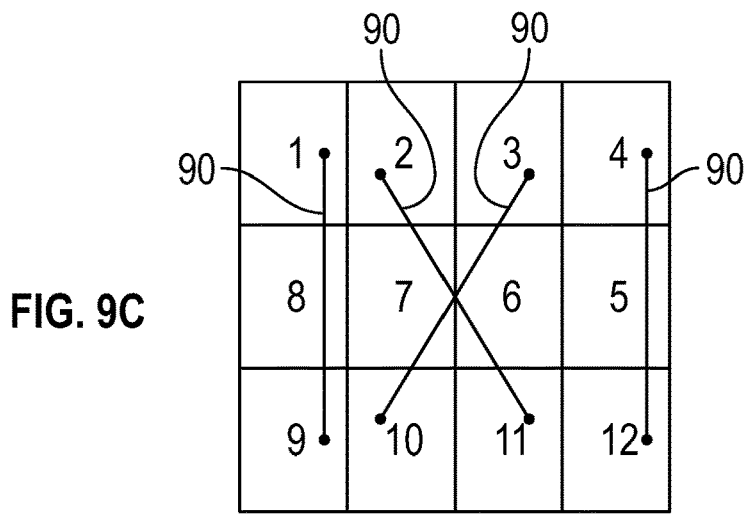
Figure 9D:
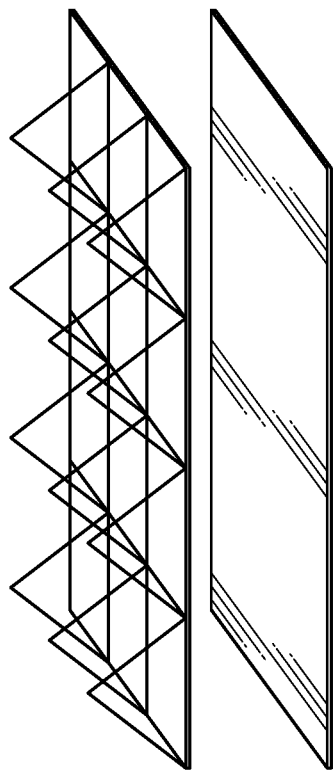
Figure 9E:
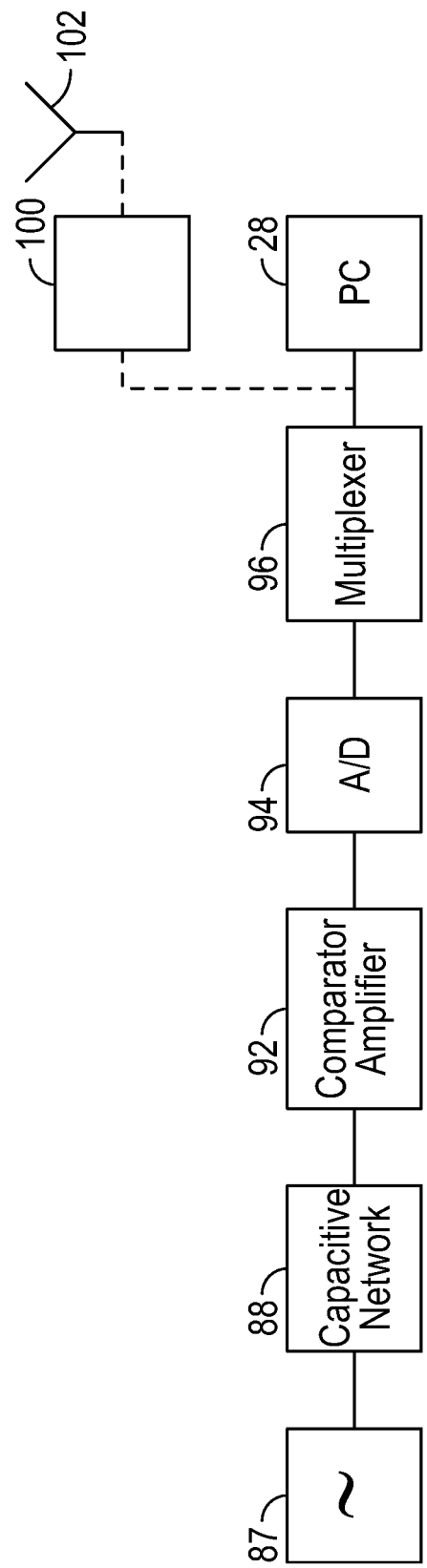
FIG. 9E is a block diagram of the electronics used in association with the swing sensors plate of FIGS. 9A-9D.

The golf club motion sensor plate 80 having a top motion plate 82 and a bottom motion plate 84 is diagrammatically shown in FIGS. 9A-D, wherein the top motion plate 82 contains a plurality of capacitor-forming electrically isolated platelets 83 (twelve platelets are illustrated in this exemplary preferred embodiment). They are evenly distributed at or just below the top plate's exterior upper surface 82. The bottom plate 84 has a homogenous electrically conductive interior surface 85 underlying the platelets 83. Each capacitive platelet 83 contained in the top motion plate 82 forms a capacitive component when the top and bottom motion plates are vertically closely spaced to form the golf club motion sensor plate. A suitable dielectric may be sandwiched between the two plates. The structure is adhesively or otherwise mechanically joined and it may be covered or coated as desired. The result is a golf club motion sensor plate 80 containing a capacitor matrix (a 3×4 capacitor matrix is illustrated in the preferred embodiment). The capacitive components 83 are connected to form a capacitive network 88 as 5 indicated in FIG. 9E.

Applying an energizing high frequency alternating electrical signal having a frequency in 1e8 range from 100 MHz to 200 MHz from an oscillator 87 to the golf club motion plate capacitive network 88 produces an electromagnetic field above the surface of each platelet 83 of the capacitive components of the motion sensor plate 80. Any object, including a golf club, passing near the surface of the energized motion plate will cause a perturbation of the electromagnetic field as illustrated by the sample possible pathways 90 across the plate in FIG. 9C. A network 92 of electrical comparator amplifiers (FIG. 9B) is connected to the capacitor network. The comparators of the network 92 are connected one to one with the capacitive elements of the capacitive network 88. The comparators of the network 88 detect voltage variations occasioned by electromagnetic field disturbance due to a golf club moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets 83 to serve as the transducer portion of the golf club motion detector.

The electrical signal from the comparative amplifier network 92 is applied to an analog to digital signal converter 94 (ADC) and the ADC digitized output signal is converted into a serial digital data stream by a multiplexer 96. This data identifies each platelet having had its field disturbed. The serial digital data can be input directly by wire from a multiplexer 96 to the computer 28 located at the site of the golf-player and golf club motion sensor plate 80, or as in the preferred embodiment, illustrated in FIG. 1, the serial data can be transmitted 100 and an antenna 102, included in the golf club motion electronic transmitter communication circuitry from FIG. 1.

The computer 28, under the control of the golf system software, will analyze the serial digital club motion signal, recognize from the transmitted signals the platelets 83 over which the club head passed and display the golf club swing motion.

Figure 10:
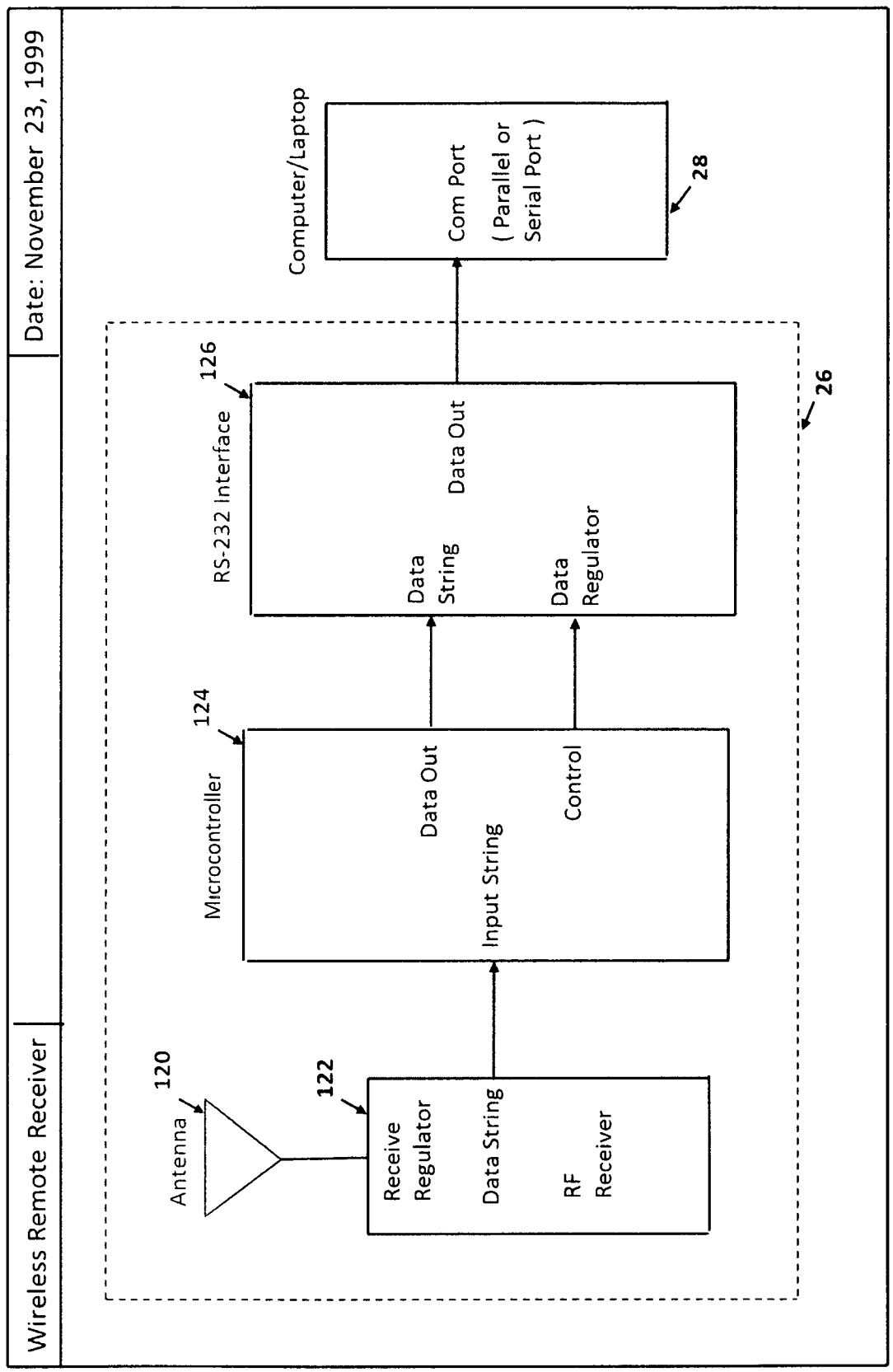
FIG. 10 is a block diagram of a computer installation for use as the computer and information receiving interconnect of the system of FIG. 1.

At each player site, a wireless radio frequency signal receiver 26 is connected to the computer 28 by either the serial (USB) or parallel computer ports, as shown in the functional block diagram, FIG. 10. The wireless signal receiver 26 detects digitally coded radio frequency transmissions from the communication circuit associated with any of a smart golf club 20, a golf ball receptacle 22, or a golf club motion sensing plate 24, as shown in FIG. 1. The received transmission are demodulated by the RF receiver circuitry 122 (FIG. 10) connected to a microcontroller 124, which converts the demodulated data signal to serial binary coded data suitable for communications to a computer 28. The computer 28, under the control of the internally installed golf system software program, monitors and directs the flow of communications between remotely located players via the internet and displays the game simulations and performance information. In appropriate installations the wireless electromagnetic signals that communicate with the receiver may be infrared communications.

Figure 11:
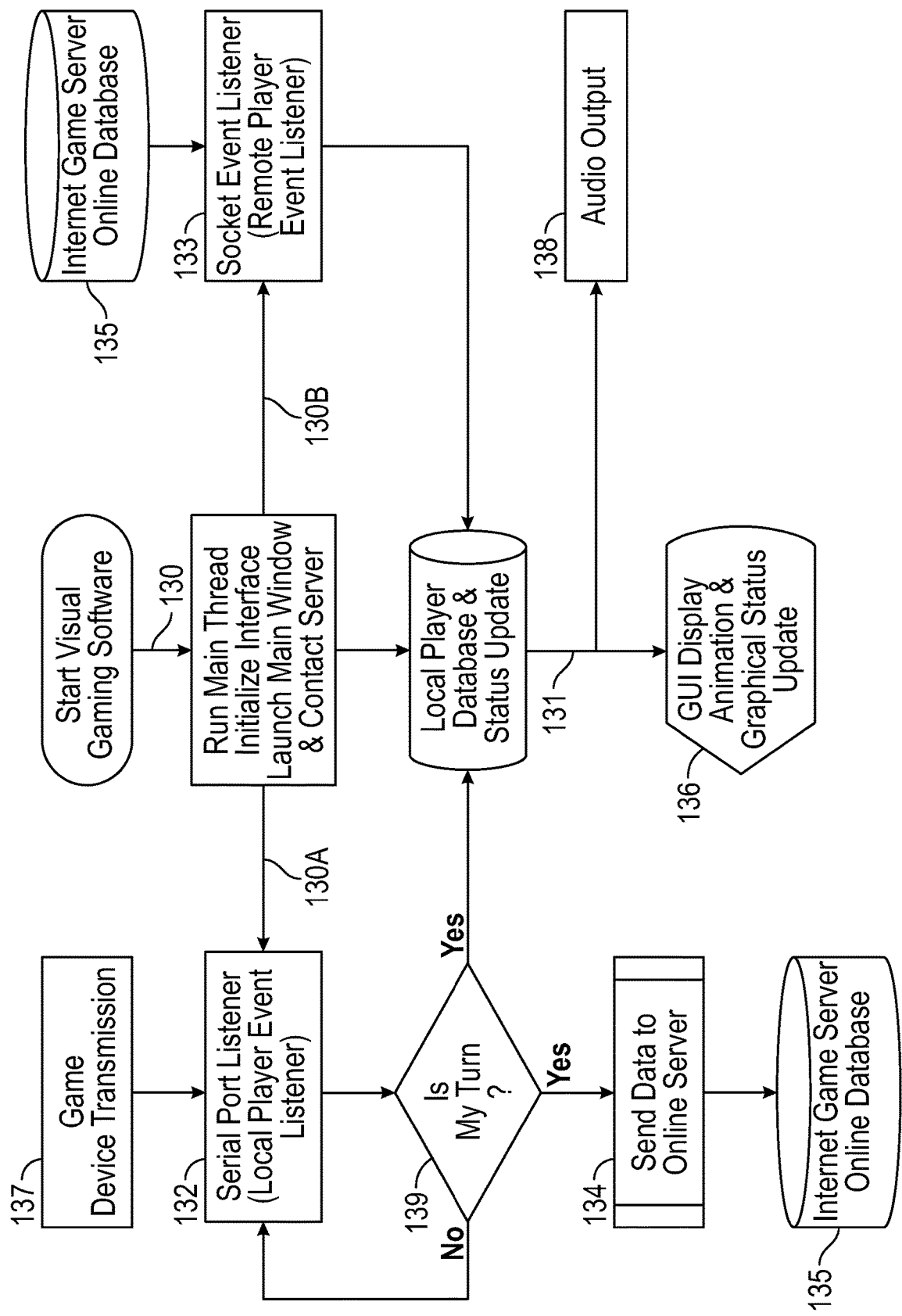
FIG. 11 is a functional block diagram of the software operation of the computer of FIG. 10.

At each remote player site, the computer 28 (FIG. 1) under the control of the golfing software program (shown in the golfing software system functional block diagram, FIG. 11) monitors and control initialization and the sequential play of the golf game, or alternatively, the individual player practice session. Upon start up by a player at a particular site, the system input parameters are set and the system internet and player port interfaces are initialized 130 as indicated by the arrows 130a and 130b. For internet communications, the serial port listener of the computer 28 is enabled in the preferred embodiment. A remote player event listener is initialized. It will communicate events from one or more of the golf club, the golf ball receptacle and the motion sensor plate. The main operational software program thread is run 130, and the system awaits data input from the appropriate computer communications ports at 132 (port), 133 (remote player Socket Event Listener).

Figure 12:
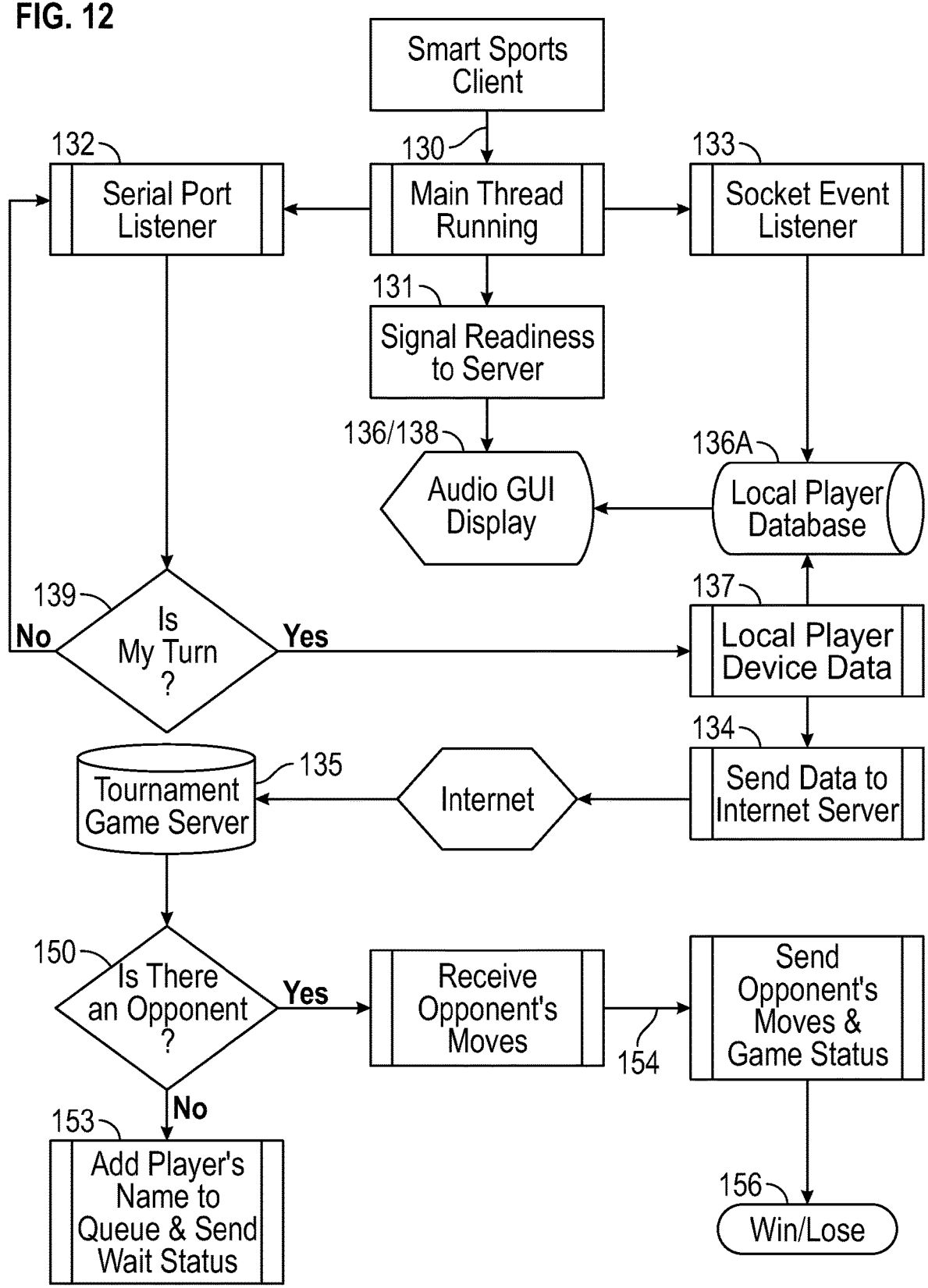
FIG. 12 is a flowchart illustrative of a portion of the operation of the computer of FIG. 10 operating as indicated in the block diagram of FIG. 11.

If the competitive play mode has been selected, the program generates a player participation request and sends 134 the request to the game Internet server (GGC server) 34 (FIG. 1). Upon identification of a player opponent at 150 (FIG. 12) by the GGC server, the program initiates the player identification sequence 152 and sequential play begins 154. This software sequence and control routine occurs at each remote site where play has been initiated. During the game play sequences 154, the program generates the appropriate animation, display, and audio data and commands 136 and 138 (FIG. 11) and communicates with the associated display and speaker devices 30 and 31 (FIG. 1). Upon the occurrence of a local computer player event, detected at 133, the main operating program at 130, displays the event at 136, and communicates the event at 132 by causing a device transmission at 137 to be sent at 134 via the internet GGC server 135 which displays the event for the opposing player and alerts the opposing player it is his/her turn to play. The local computer player event may be, but is not limited to, the (smart) golf club impacting a ball, the swing of a club across the sensing plate or the ball's entry into the receptacle. The program contains time delay limits for the player action, and delays of play beyond these limits generate play quit and disconnect signals.

The event at 133 also has the effect of indicating at 139 that it is no longer the local player's turn and enables (as indicated by line 139) the serial port listener at 132 to detect an event from the remote computer player, again via the Internet.

If the single player practice mode is selected, the Internet communications sequences are disabled, other software sequential operating routines continue as above described and the player's golf club stroke, ball-receptacle contact, and/or dub swing motion sensor information are communicated only to the computer located at the player's site and the performance information is analyzed and displayed only at the local computer player's site.

Figure 13:
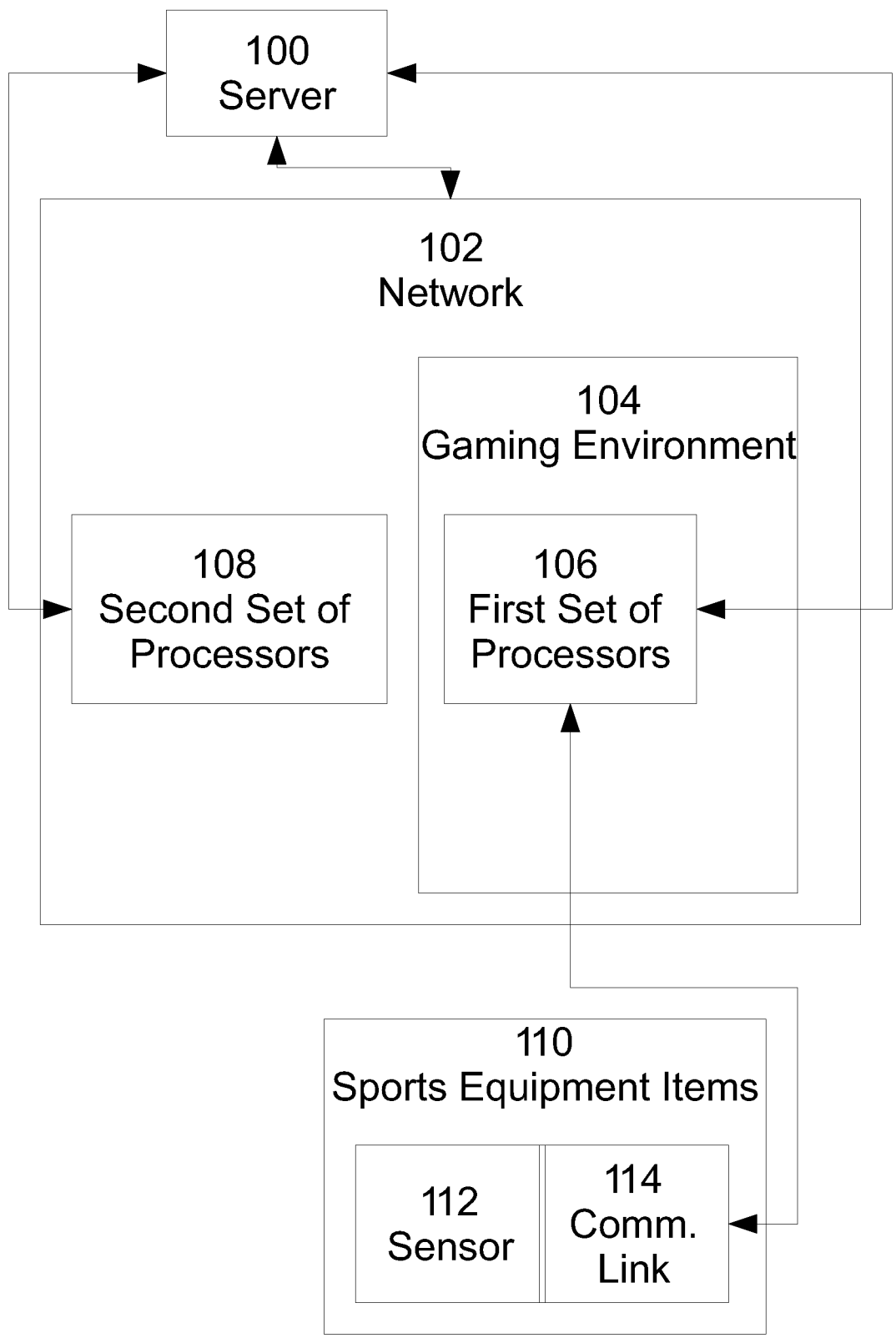
FIG. 13 features an exemplary system diagram.

When a game is won, lost, or terminated, the golf software system generates the appropriate output signals 156 (FIG. 12), displays the player performance information, and resets to initial pre-game conditions. If one player opponent quits the game or is 'timed out" (due to excessive delay in play) and the remaining player wishes to continue play, the software resumes an internal search for another opponent 152 and 153. Using programming as contained in the accompanying microfiche appendix, one skilled in the art can readily accomplish the game programming described. Alternative programming will be apparent from the foregoing functional description and the illustrations contained in the appended drawings As shown in FIG. 13, the system comprises a server 100 via a network 102 to a first set of processors 106 within a gaming environment 104 and a second set of processors 108 outside the gaming environment. The first set of processors are connected via communication links 114 to sports equipment items 110. The communication links are integrated into or connected to sensors 112 that record or receive various data from the sports equipment items, such as physiological data, location data, position data, velocity data, energy data, proximity data, angle data, etc.

Figure 14:
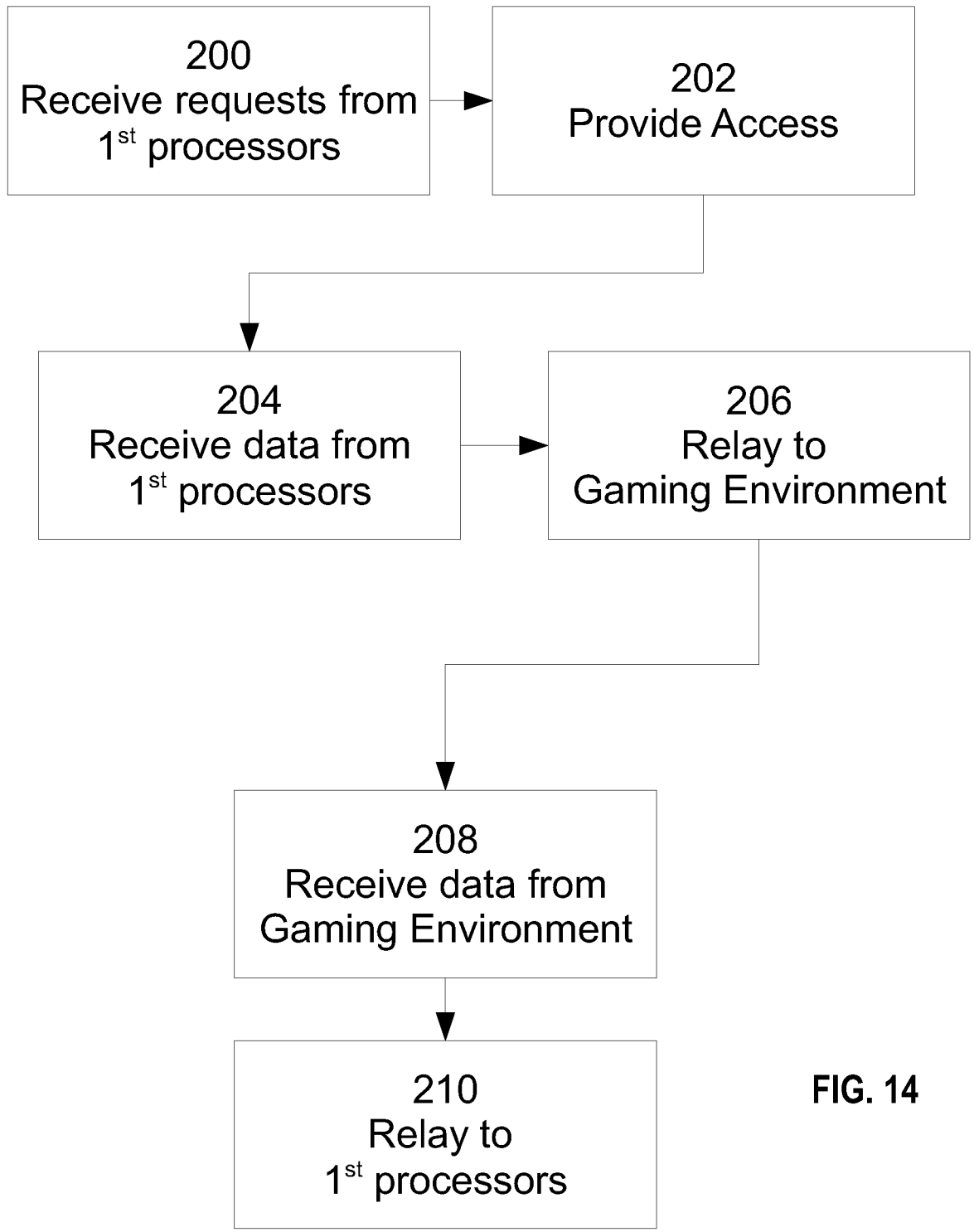
FIG. 14 features an exemplary system flowchart.

As shown in FIG. 14, the server is programmed 200 to receive requests from a first set of processors to access the gaming environment and then 202 provide access. The server may receive data from the first set of processors 204 and relay that data 206 to the other processors in the gaming environment. Similarly, the server may receive data from other processors in the gaming environment 208 and relay them to the first set of processors 210.

Figure 15:
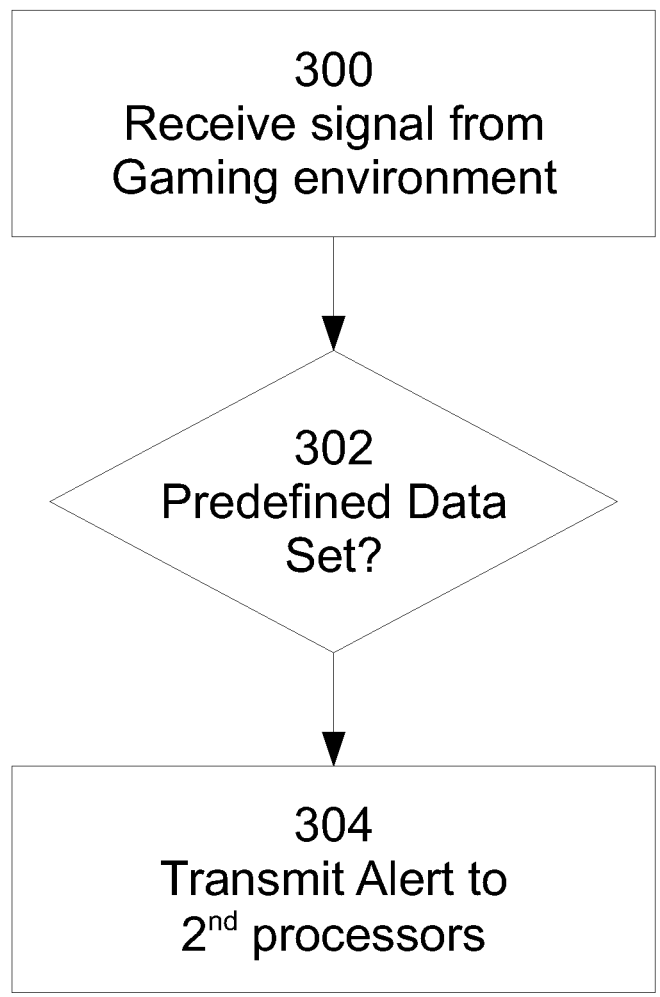
FIG. 15 features an exemplary system flowchart.

As shown in FIG. 15. The server is programmed to receive signals from the gaming environment 300, determine if the signals contain a predefined data set 302, and if so, transmit an alert or message to the second set of processors 304.

The invention claimed is:

1. A system comprising a game server, local computers connected over a network, and gaming equipment, the gaming equipment comprising sensors and communications links configured to obtain movement and position information, said sensors being embedded contact sensors producing detectable variances representing the magnitude and duration of the contact forge applied on the contact sensors and the proximate location of such contact relative to the preferred location on the face of the gaming equipment, the communications links configured to transfer the movement and position interactive information over the network to hie game server.

2. The system of claim 1, the local computers connected to displays and programmed to receive graphic data from the game server and display player performance graphics.

3. The system of claim 1, the game server configured to direct communications between players from remote sites over the network.

4. The system of claim 1, the local computers programmed to simulate and display local and remote game events.

5. The system of claim 4, the game server configured to control an initialization and sequential play of opposing players, measure player time delays, and generating play quit and disconnect signals.

6. The system of claim 5, the local computer programmed to receive graphic data from the game server and display player performance graphics on displays.

7. The system of claim 1, the local computers programmed to generate a player participation request transmit it over the network to the game server, the game server configured to identify opponent players, determine player readiness to participate in the internet game competition, and pair players together in order to play.

8. The system of claim 7, the game server configured to transmit graphic data to the local computers, the local computers programmed to display player performance graphics on displays.

9. The system of claim 8, the local computers programmed to simulate and display local and remote game events on the displays.

10. The system of claim 1, the game server configured to control an initialization and sequential play of game players and transmit an alert to an opposing player that it is their turn to play.

11. A method of providing remote players access to an internet game competition comprising the steps of attaching sensors and communication links to gaming equipment and wirelessly transmitting information obtained from the sensors over a network via the communication links to a game server, said sensors being motion sensors producing varying characteristics representing the velocity, angle, and proximity of a gaming equipment to the surface of the motion sensors, the information relating to movement and position of the gaming equipment.

12. The method of claim 11 comprising the additional step of transmitting graphic data from the game server to local computers and displaying player performance graphics on displays connected to the local computer.

13. The method of claim 11, comprising the additional step of directing communications between players tom remote sites over the network.

14. The method of claim 11, comprising the additional step of simulating and displaying local and remote game events.

15. The method of claim 11, comprising the additional steps of generating a player participation request, transmitting it over the network to the game server, identifying opponent players, determining player readiness to participate in the internet game competition, and paring players together in order to play.

16. The method of claim 15, comprising the additional steps of controlling an initialization and sequential play of opposing players, measuring player time delays, and generating play quit and disconnect signals.

17. The method of claim 16, comprising the additional step of transmitting graphic data from the game server to local computers and displaying player performance graphics on displays connected to local computers.

18. The method of claim 11, comprising the additional step of controlling an initialization and sequential play of game players and transmitting an alert to an opposing player that it is their turn to play.

19. A method of providing remote players access to an internet game competition comprising the steps of providing a set of local computers and a game server, attaching sensors and communication links to gaming equipment said sensors being noncontact sensors, wirelessly connecting the communication links to the local computers, capturing varying characteristics representing the velocity, angle, and proximity of the gaming equipment to the surface of the noncontact sensors, and transmitting information obtained from the sensors over a network from the local computers to hie game server.

20. The method of claim 19, comprising the additional steps of transmitting graphic data from the game server to the local computers and displaying player performance graphics on displays connected to the local computers.

21. The method of claim 20, comprising the additional steps of simulating and displaying both local and remote game events on the displays.

* * * * *

UNITED STATES PATENT AND TRADEMARK OFFICE
CERTIFICATE OF CORRECTION

PATENT NO. : 10,653,964 B2  
APPLICATION NO. : 15/466569  
DATED : May 19, 2020  
INVENTOR(S) : Wilbert Q. Murdock and Philip A. Williams Page 1 of 3

It is certified that error appears in the above-identified patent and that said Letters Patent is hereby corrected as shown below:

In the Specification

Column 1, Line 38, "equipment items" should read --equipment items and sports implements--;

Column 2, Line 62, "computer processor" should read --processor, or a computer processor--;

In the Claims

Claim 1, Column 10, Line 13, "communications" should read --communication--;

Claim 1, Column 10, Line 15, "being" should read --comprise--;

Claim 1, Column 10, Line 17, "the magnitude" should read --a magnitude--;

Claim 1, Column 10, Line 17, after "contact" delete "forge" and insert --force--;

Claim 1, Column 10, Line 19, after "gaming equipment," insert --wherein--;

Claim 1, Column 10, Line 20, "communications" should read --communication--;

Claim 1, Column 10, Line 20, after "configured to transfer" delete "the";

Claim 2, Column 10, Line 23, after "claim 1," insert --wherein--;

Claim 3, Column 10, Line 26, after "claim 1," insert --wherein--;

Claim 3, Column 10, Line 26, after "game server" insert --is--;

Claim 4, Column 10, Line 29, after "claim 1," insert --wherein--;

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,653,964 B2

Claim 4, Column 10, Line 29, after "local computers" insert --are--;

Claim 5, Column 10, Line 32, after "claim 4," insert --wherein--;

Claim 5, Column 10, Line 32, after "game server" insert --is--;

Claim 6, Column 10, Line 36, after "claim 5," insert --wherein--;

Claim 6, Column 10, Line 36, after "local computer" insert --is--;

Claim 7, Column 10, Line 39, after "claim 1," insert --wherein--;

Claim 7, Column 10, Line 39, after "local computers" insert --are--;

Claim 7, Column 10, Line 40, after "request" insert --and--;

Claim 8, Column 10, Line 45, after "claim 7," insert --wherein--;

Claim 9, Column 10, Line 49, after "claim 8," insert --wherein--;

Claim 9, Column 10, Line 49, after "local computers" insert --are--;

Claim 10, Column 10, Line 52, after "claim 1," insert --wherein--;

Claim 10, Column 10, Line 52, after "game server" insert --is--;

Claim 11, Column 10, Line 61, "being" should read --comprising--;

Claim 11, Column 10, Line 63, after "equipment" insert --item--;

Claim 11, Column 10, Line 64, after "movement and" insert --/ or--;

Claim 12, Column 10, Line 66, "claim 11" should read --claim 11,--;

Claim 12, Column 10, Line 66, "step" should read --steps--;

Claim 12, Column 11, Line 2, "local computer" should read --local computers--;

Claim 13, Column 11, Line 4, after "players" delete "torn" and insert --to--;

Claim 14, Column 11, Line 7, after "additional" delete "step" and insert --steps--;

Claim 14, Column 11, Line 7, after "local and" insert --/ or--;

Claim 15, Column 11, Line 11, "it" should read --the player participation request--;

CERTIFICATE OF CORRECTION (continued)
U.S. Pat. No. 10,653,964 B2

Claim 15, Column 11, Line 14, before "players" delete "paring" and insert --pairing--;

Claim 16, Column 11, Line 17, delete "an" after "controlling";

Claim 17, Column 11, Line 21, "step" should read --steps--;

Claim 18, Column 12, Line 2, after "additional" delete "step" and insert --steps--;

Claim 18, Column 12, Line 2, delete "an" after "controlling" and insert --the--;

Claim 19, Column 12, Line 8, "gaming equipment" should read --gaming equipment,--;

Claim 19, Column 12, Line 9, "being" should read --comprising--;

Claim 19, Column 12, Line 14, delete "hie" before "game server" and insert --the--.